United States Patent
Magne-Drisch et al.

(10) Patent No.: US 6,376,734 B1
(45) Date of Patent: Apr. 23, 2002

(54) PROCESS FOR THE PRODUCTION OF AT LEAST ONE ISOMER OF XYLENES THAT COMPRISE AN ADSORPTION STAGE AND AN ISOMERIZATION STAGE WITH AN EUO-STRUCTURAL-TYPE CATALYST

(75) Inventors: Julia Magne-Drisch, Vilette de Vienne; Gérard Hotier, Rueil Malmaison; Alain Methivier, Orleans; Jean-Francois Joly, Lyons; Fabio Alario, Neuilly sur Seine; Elisabeth Merlen, Rueil Malmaison, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/598,646

(22) Filed: Jun. 22, 2000

(30) Foreign Application Priority Data

Jun. 22, 1999 (FR) .............................. 99 07968

(51) Int. Cl.⁷ .............................. C07C 7/00; C07C 7/12
(52) U.S. Cl. .................. 585/805; 585/822; 585/825; 585/828
(58) Field of Search .................. 585/805, 822, 585/825, 828

(56) References Cited

U.S. PATENT DOCUMENTS

| | | | |
|---|---|---|---|
| 4,341,914 A | 7/1982 | Berger | 585/474 |
| 4,537,754 A * | 8/1985 | Casci et al. | 423/277 |
| 4,783,568 A | 11/1988 | Schmidt | 585/477 |
| 5,629,467 A * | 5/1997 | Hotier et al. | 585/805 |

FOREIGN PATENT DOCUMENTS

| | | |
|---|---|---|
| EP | 0 051 318 | 5/1982 |
| EP | 0 923 987 | 6/1999 |
| EP | 0 923 987 A1 | 6/1999 |
| FR | 2 768 724 | 3/1999 |
| JP | 50-16780 * | 6/1975 |

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

A process for the production of at least one isomer of xylenes comprising a simulated moving-bed adsorption (8) of a C8-aromatic feedstock (1) that delivers a paraxylene-rich fraction (9) that is optionally purified after a distillation (16) by at least one high-temperature crystallization (5) and a fraction (10) that is low in paraxylene is described. Fraction (10) is distilled and then isomerized (21) in the presence of an EUO-structural-type catalyst. The lightest hydrocarbons are removed from the isomerization effluent in a first distillation (23) then naphthenes in a second distillation (26), and distilled isomerization effluent (2) that results therefrom is recycled at least in part in adsorption (8). A mother liquor (3) that results from the crystallization stage is recycled at least in part in adsorption (8).

21 Claims, 1 Drawing Sheet

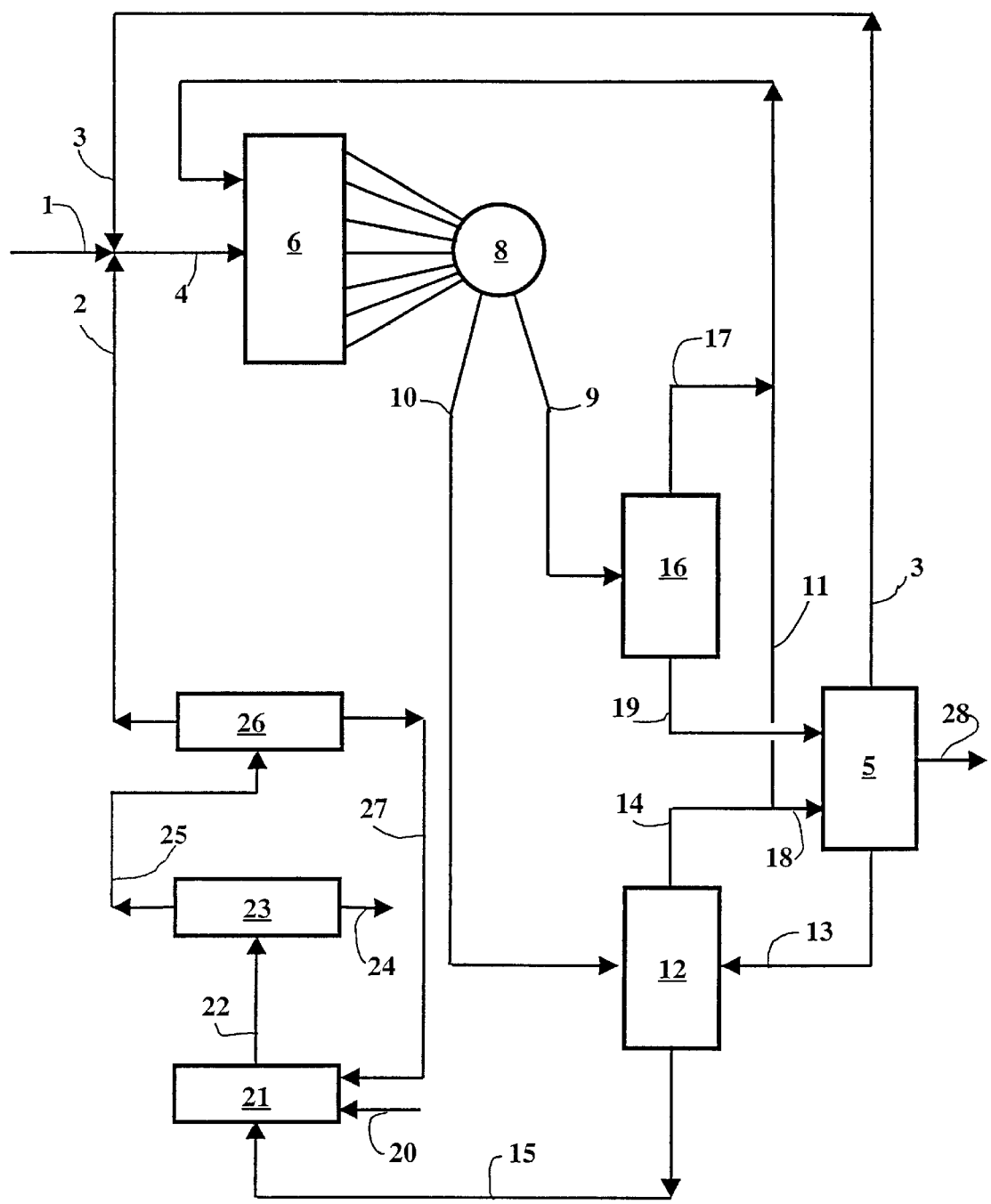

PROCESS FOR THE PRODUCTION OF AT LEAST ONE ISOMER OF XYLENES THAT COMPRISE AN ADSORPTION STAGE AND AN ISOMERIZATION STAGE WITH AN EUO-STRUCTURAL-TYPE CATALYST

CROSS-REFERENCE TO RELATED APPLICATION

This application is related to Applicants' concurrently filed U.S. application Ser. No. 09/598,486, entitled "Process For The Production Of An Isomer Of Xylenes In Three Stages: Separation, Isomerization In The Presence Of A Catalyst Based On An EUO Zeolite And Transalkylation", based on French Application 99/07.967 filed Jun. 22, 1999 and U.S. Ser. No. 09/598,651, entitled "Production Of A Xylene Isomer In Three Stages: Separation, Isomerization With A Catalyst With An EUO Zeolite Base And Transalkylation With Recycling Of C10-Aromatic Compounds", based on French Application 99/07.966 filed Jun. 22, 1999.

The invention relates to a process for the production of at least one isomer of xylenes, from a C8-aromatic fraction, whereby said process comprises the scheme of a separation stage by adsorption in a simulated moving bed of paraxylene or of a mixture of orthoxylene and metaxylene or metaxylene or ethylbenzene, and an isomerization stage of the fraction that is low in the desired isomer.

The prior art is illustrated by Patent Application FR-768 724 of the applicant.

Although the principle of the combination of an adsorption stage in a simulated moving bed and an isomerization stage, as well as the one that preferably consists in carrying out, in particular in the case of paraxylene, at least one crystallization stage, is already described in the prior art, the fact of using in the isomerization process an isomerization catalyst that comprises at least one EUO-structural-type zeolite, for example the EU-1 zeolite, and at least one element of group VIII of the periodic table makes it possible to improve, surprisingly enough, the productivity of the scheme and to reduce its losses. In a preferred embodiment of the invention, an adsorbent that incorporates a zeolitized binder that has a high adsorption capacity will be used in the adsorption stage. According to a variant of the invention, in the adsorption process, the injection of small amounts of water with the desorbent makes it possible to reduce the solvent level. Finally, according to another variant of the invention, a recrystallization stage on the mother liquor is carried out in the crystallization process.

The combination of this variety of variants makes it possible to improve, surprisingly enough, the productivity of the scheme and to reduce its losses by synergy effects.

The production of a specific isomer of the xylenes is an important petrochemical process in the synthesis of the polyesters, used in particular in the fabric manufacturing industry. It is then important to be able to synthesize the desired isomer, preferably the paraxylene with maximum purity. Several techniques for separating isomers have been developed. Thus, the separation of the isomers can be done by adsorption, for example in a zeolitic sieve, that delivers a fraction that is very high in paraxylene and a fraction that is low in paraxylene and therefore high in particular in orthoxylene and metaxylene, in the presence of an elution solvent. Since the composition of the aromatic feedstocks with eight carbon atoms varies broadly, however, according to their origin, with the para and ortho isomer content generally coming close to 50%, a single process does not make it possible to maximize the production of the desired isomer, such as, for example, paraxylene. It then is necessary to combine an adsorption stage of the feedstock followed by an isomerization stage of this fraction that is low in desired isomer as is described in, for example, Patent GB 1,420,796. Patent EP 531 191 of the applicant describes a process for the production of paraxylene by treatment in an adsorption zone that is followed by at least one stage for crystallization of the adsorbed paraxylene, whereby the raffinate that is low in paraxylene is sent into an isomerization zone.

In U.S. Pat. No. 5,401,476 of the applicant, the described combination is a scheme of:

1. a process for separation of paraxylene in a simulated moving bed preferably with a small number of beds where an effort is made to obtain primarily a very high productivity and a small solvent level at the expense of the purity, a first fraction that is high in paraxylene and toluene and a second fraction that is high in other C8-aromatic isomers and that contains toluene are obtained,
2. a first distilling column that can separate paraxylene from toluene,
3. a second distilling column that can separate the other C8-aromatic isomers from toluene,
4. a crystallization that makes it possible, starting from paraxylene with a purity of between 75% and 98%, to produce paraxylene of commercial purity (at least 99.5%) and a mother liquor that is recycled in part in stage 15) of an isomerization that treats the mixture of other C8-aromatic isomers to produce paraxylene in thermodynamic equilibrium with other C8-aromatic isomers, then after elimination of the light components that are produced during the isomerization, recycling in stage 1.

The three main stages that are described in the prior art were greatly improved by the applicant; as a result, by a synergy effect, the combination became much more productive and the relative values of the different flows have very little to do with the values that are provided in the examples of U.S. Pat. No. 5,401,476.

The adsorption stage was improved with regard to the ratio of feedstock flow rate to solvent flow rate as described in French Patent 2,757,507 by the injection of water with a controlled content: instead of a solvent level on the order of 1.35/1, the injection of water either in the desorbent stream or in the feedstock stream to obtain a weighted water mean on the outlets of about 80 ppm in the case of an adsorbent with an X zeolite base that is exchanged with barium and about 10 ppm in the case of a Y zeolite that is exchanged with barium and potassium made it possible to reduce, for example, the solvent level to 1/1 in the first case and 1.2/1 in the second case.

The adsorption stage has also been improved with regard to its monitoring and its stability: U.S. Pat. Nos. 5,578,215 and 5,578,216 teach how to compensate the volume differences from bed to bed and in particular the one that is created by the recycling pump or by the production of a shorter bed for the stage that is integral with the recycling pump, or by the desynchronization of the switching times of the various flows to compensate for the delays or advances of the elution fronts. In contrast, French Patent 2,762,793 of the applicant shows how, starting from at least one analysis point of the internal concentration profile, it is possible to monitor the inside ratios of the liquid flow rates with solid flow rates to remain permanently at peak performance levels despite the inevitable fluctuations of flow rate and composition of the feedstock that is to be separated.

The adsorbent itself was greatly improved by using a particular binder that it is possible to transform at least in part into a zeolite after the shaping and either before or after the ion exchange. In this way, the adsorption capacity is increased by at least 15% (FR 99/02151). In contrast, by using a very particular X zeolite, with an Si/Al ratio that is close to 1, it is possible to increase the adsorption capacity even more (FR-A-2 767 524).

In French Patent Application FR 2729660, the applicant showed more specifically how a second crystallization stage that is carried out on the mother liquor that exits the first crystallization makes it possible to increase the yield of the crystallization and to reduce significantly the recycling flow rate of mother liquor to the adsorption stage.

For the isomerization stage, the catalyst that is used in the isomerization reactions is generally the mordenite that is mixed with other zeolites, such as the ZSM-5 zeolite, as described in U.S. Pat. Nos. 4,467,129; 4,482,773 and EP 138 617 B. Other catalysts have a mordenite base and have been described in, for example, U.S. Pat. Nos. 4,723,051; 4,665, 258 and FR 2,477,903.

Catalysts for isomerization of the C8-aromatic fractions with a base of EUO-structural-type zeolites, i.e., the EU-1, TPZ3 and ZSM-50 zeolites, were described by the applicant in Patent Applications FR-A- 2 772 642 and FR-A- 2 772 752, incorporated as references.

The object of the invention is to eliminate the drawbacks of the prior art by proposing an optimized solution in which the productivity is increased and the losses are reduced. Another object of the invention is to describe a hybrid process for the production and separation of paraxylene with a productivity that is greater than the one that is obtained with the processes of the prior art and whose losses are reduced with the use of a more selective isomerization catalyst and preferably with reduced recycling owing to the implementation of a set of special means described below. Within the meaning of this description, hybrid process refers to a process that comprises at least one crystallization stage that is downstream from the adsorption zone.

The process according to this invention makes it possible, surprisingly enough, to obtain yields of paraxylene that are much higher than those of the prior art with improved performance levels in activity and selectivity during the isomerization stage, which further brings about a reduction of the recycling volumes as well as a reduction in size of the recovery zone of the paraxylene. Actually, the process according to this invention makes it possible to limit the losses during the isomerization stage, with the use of a catalyst that comprises an EUO-structural-type zeolite. In addition, the stability of the isomerization catalyst is improved relative to the catalysts of the prior art. Also, the various improvements that are made in the separation zone make it possible to increase the productivity of the process significantly.

The invention relates to a process for the conversion of hydrocarbons and for the production of at least one isomer of xylenes that is selected from among orthoxylene, paraxylene and metaxylene with a yield of desired isomer that is improved relative to the processes of the prior art with the use in the isomerization zone of a catalyst with an EUO-structural type zeolite base and at least one metal of group VIII of the periodic table. This process can preferably use an adsorbent that incorporates a zeolitized binder in the separation zone. According to another implementation of the process, it is possible to inject small amounts of water with the desorbent into the adsorption zone. This process preferably uses a recrystallization stage on the mother liquor in the crystallization zone that most often comprises an arrangement of several stages, under rigid temperature and pressure conditions that make it possible to obtain optimal operation of the unit.

More specifically, the process for production of at least one xylene isomer of this invention in general comprises the following stages:

a) In at least one simulated moving-bed adsorption zone, a feedstock that contains aromatic compounds with eight carbon atoms, i.e., metaxylene, paraxylene, ethylbenzene and orthoxylene, is brought into contact continuously with a zeolitic adsorbent bed in the presence of a suitable desorption solvent, under adsorption conditions such that a first fraction that contains solvent and that is high in desired isomer and a second fraction that is low in desired isomer and that comprises the majority of the other isomers and solvent are obtained. The first fraction will contain, for example, paraxylene with a purity of between 75 and 99.9%. The second fraction will then contain metaxylene, ethylbenzene and optionally orthoxylene, b) the first fraction is distilled to separate the solvent, on the one hand, and the desired isomer, on the other hand, c) the second fraction that is low in desired isomer is distilled, and the solvent, on the one hand, and the majority of the other isomers, on the other hand, are recovered, d) the fraction that contains the majority of the other isomers recovered in stage c) is isomerized under suitable conditions in the presence of hydrogen in an isomerization zone, and an isomerate is recovered that is preferably at least in part recycled to stage a) after having generally eliminated the light compounds (with a boiling point that is less than 80° C.), and fraction 80–135° C. that is recycled, for example, at the inlet of the isomerization zone, whereby said process is characterized in that the isomerization reaction that is described in stage d) is implemented in the presence of a catalyst that comprises at least one EUO structural-type zeolite and at least one element of group VIII of the periodic table.

According to a preferred embodiment of the process according to this invention, it is possible to use at least one crystallization zone downstream from the adsorption zone. Thus, in the case where the desired isomer is paraxylene, at least one crystallization of the paraxylene of stage b) is initiated in at least one crystallization zone at a temperature of between +10° C. and −25° C., and, on the one hand, a mother liquor is obtained that can be recycled at least in part to stage a) and, on the other hand, paraxylene crystals that are saturated with mother liquor are obtained.

According to a preferred embodiment of the process according to this invention, it is possible to wash in a washing zone with a suitable washing solvent the crystals of the isomer that is desired, and these crystals are recovered. In the case where the desired isomer is paraxylene, the paraxylene crystals with a very high degree of purity, or generally at least 99.6% and preferably at least 99.8%, are recovered.

Thus, the catalyst that is used in the isomerization stage comprises at least one EUO zeolite, i.e., the EU-1, TPZ-3 and ZSM-50 zeolites.

The EUO-structural-type EU-1 zeolite, already described in the prior art, has a monodimensional microporous network, whose pore diameter is 4.1×5.7 Å (1 Å=1 angstrom=$1.10^{-10}$ m) ("Atlas of Zeolites Structure Types," W. M. Meier and D. H. Olson, 4th Edition, 1996). In contrast, N. A. Briscoe et al. taught in an article of the journal Zeolites (1988, 8, 74) that these monodimensional channels have side pockets with a depth of 8.1 and a diameter of 6.8×5.8 Å. The synthesis method of the EU-1 zeolite and its physico-chemical characteristics were described in Patent EP-42 226.

U.S. Pat. No. 4,640,829 relates to the ZSM-50 zeolite, which has the EUO-structural type according to the "Atlas of Zeolites Structure Types," W. M. Meier and D. H. Olson, 4th Edition, 1996.

Patent Application EP-51 318 relates to the TPZ-3 zeolite, which has the EUO-structural type according to the "Atlas of Zeolites Structure Types," W. M. Meier and D. H. Olson, 4th Edition, 1996.

In a preferred embodiment, this invention is also characterized in that the adsorbent comprises an X zeolite or a Y zeolite that is shaped with a binder such as a clay, for example, kaolin, that can be transformed into zeolite under special conditions of temperature, pressure and pH. After the transformation of at least 50% of the binder into zeolite, an exchange, for example, with barium ions or with strontium ions in the case of the X zeolite and, for example, with potassium ions and then barium in the case of the Y zeolite, is carried out.

According to a preferred embodiment, this invention is also characterized in that the adsorbent can have a higher grain size than in the prior art, and the adsorption temperature is a little higher. Actually, the adsorbent that is described in particular in the examples of U.S. Pat. No. 5,401,476 has a grain size of a spherical shape of 0.3 to 0.5 mm of diameter, which causes significant pressure drops. With a larger spherical-shaped grain size that is 0.4.to 0.8 mm in diameter, centered on 0.65 mm of diameter and a slightly higher adsorption temperature (160 to 170° C.) to compensate for a more difficult material transfer, a pressure drop of about 2.5 times less per unit of length is obtained, and it is possible to use support beams of the distributor panels, whereby distributor panels and a ring have to meet fewer mechanical constraints, i.e., in terms of thickness and reduced cost. In contrast, the consumption of electricity of the recycling pump is also greatly reduced.

Still according to a preferred embodiment, this invention is also characterized in that it is possible to inject water into the adsorption zone, preferably with desorbent, to monitor the water content on the weighted mean of the flow rates of extract and raffinate, whereby this weighted mean depends, of course, on the type of zeolite that is used. It is also possible to reduce the solvent level relative to the feedstock.

According to another preferred embodiment of this invention (hybrid process), it is possible to use a unit of adsorbent beds that are placed inside a single column whose number usually varies from 9 to 15 according to the composition of the feedstock. For a feedstock that is easy to treat, comprising 24%, for example, of paraxylene and on the order of 4% of ethylbenzene, the number of beds is, for example, 10; for an average feedstock, for example, that comprises 22% of paraxylene and 10% of ethylbenzene, the number of beds is, for example, 12; finally for the most difficult feedstocks, for example, 17% of paraxylene and 30% of ethylbenzene, the number of beds is, for example, 15.

For the adsorption process that does not comprise (a) final crystallization stage(s), usually a set of adsorbent beds, placed inside two or more columns, whose number usually varies from 16 to 30 (24 beds, for example, for the production of paraxylene of 30 beds, for example, for the co-production of paraxylene and metaxylene) are used.

In a particular implementation of the invention, the first or the last bed of each column (depending on the valve system that allows the introduction or the draw-off of fluids) can have a small volume to compensate approximately the volume of the recycling loop: this compensation is such that all of the non-selective volumes of this bed added to the volume of the recycling loop is approximately equal to the non-selective volume of an intermediate bed. Once the unit is produced, the calculation of the amounts of adsorbent charged bed by bed makes it possible to compensate for which each of the flows is connected to each of the beds, in each case because of non-selective volumes of each of the beds. This correction technique is only possible, of course, provided that one all-or-nothing valve is used per bed and per flow. Once the unit is operational, on-line analyses are carried out continuously (by a Raman spectrometer, for example, as described in U.S. Pat. No. 5,569,808) or intermittently by a vapor phase chromatograph on the recycling loop. By knowing, on the one hand, the concentration profile and, on the other hand, the internal flow rates and the mean switching time, ratios of the liquid flow rate s to the solid flow rate or else the eluted volumes in each zone are calculated during a period that is used as a control variable for maximizing the purity and the yield continuously.

The separation zone comprises at least one adsorption zone in which is adsorbed the majority of the desired isomer or the majority of undesirable isomers. In an implementation of the invention, the separation zone makes it possible to recover paraxylene, i.e., paraxylene is adsorbed and recovered as an extract. other implementations of the invention make it possible to recover metaxylene and orthoxylene based on the selected adsorbent. The adsorption zone operates in a simulated moving bed and comprises at least one zeolitic adsorbent bed that operates in the presence of a suitable desorption solvent and under adsorption conditions such that there is obtained, in the case where an attempt is made to recover paraxylene, a first fraction that contains solvent, metaxylene, ethylbenzene, and orthoxylene, and a second fraction essentially of paraxylene and solvent. The paraxylene that is obtained generally has a purity of between 75 and 98% in the case of the hybrid process and 99.6 to 99.9% in the case of the process without crystallization. The first fraction is distilled to recover the paraxylene, on the one hand, and the solvent, on the other hand, and the second fraction is distilled to separate the solvent, on the one hand, and the mixture of metaxylene, orthoxylene and ethylbenzene, on the other hand. The second fraction is then sent into the xylene isomerization zone. The solvent can be recycled at the inlet of the separation zone.

The simulated moving bed can be a simulated counter-current bed or a simulated co-current bed. The elution solvent or desorption solvent is selected, for example, from among toluene or paradiethylbenzene. This list is nonlimiting, and other solvents such as methyl-tert-butyl ether (MTBE) or diisopropyl ether (DIPE) can also be used.

The adsorbents that make it possible to adsorb the paraxylene selectively comprise at least one zeolite that is selected from among the X and Y zeolites of which most often the exchangeable sites are occupied by alkaline or alkaline-earth cations, such as, for example, potassium and barium.

The adsorbents that make it possible to adsorb the metaxylene and the orthoxylene selectively are, for example, the X or Y zeolites that are exchanged with, for example, at least one of the following metals: Li, Na, Be, Mg, Ca, Sr, Mn, Cd, Cu., Ni.

The xylene separation zone can preferably comprise at least: one crystallization zone downstream from the adsorption zone. Thus, for example, the paraxylene that is recovered after distillation of said second fraction is sent into at least one crystallization zone at a temperature of between, for example, +10 and −25° C., and, on the one hand, a mother liquor is obtained that is preferably recycled to the adsorption zone, and, on the other hand, paraxylene crystals that are saturated with mother liquor are obtained, then it is washed with a suitable washing solvent to obtain paraxylene crystals with a very high degree of purity, or generally purity of greater than 996% and preferably greater than 99.8%.

A preferred two-stage crystallization process was described by the applicant in Patent Applications WO 96/20907, WO 96/20908 and WO 96/22262.

As solvent for washing crystals, it is possible to use, for example, n-pentane, water, purified paraxylene or toluene. The same solvent is preferably used for desorption and for washing crystals, such as, for example, toluene, or else purified paraxylene to avoid having to redistill the last traces of washing solvent.

The first distilled fraction that is recovered after the xylene separation stage that comprises orthoxylene, metaxylene and ethylbenzene is treated in an isomerization zone. Isomerization stage c) is implemented in the presence of a catalyst that comprises an EUO-structural-type zeolite, for the EU-1 zeolite. The EUO-structural-type zeolite is at least in part in acid form and comprises silicon and at least one element T that is selected from the group that is formed by aluminum, iron, gallium and boron, preferably aluminum and boron, with an overall Si/T atomic ratio that is greater than 5.

The EUO-structural-type zeolite, for the EU-1 zeolite, in the catalyst according to the invention, can be at least in part, preferably virtually totally, in acid form, i.e., in hydrogen form ($H^+$), whereby the sodium content is preferably such that the Na/T atomic ratio is less than 0.5, preferably less than 0.1, even more preferably less than 0.02.

The catalyst also comprises at least one matrix that comprises at least one compound that is selected from the group that is formed by clays, magnesia, aluminas, silicas, titanium oxide, boron oxide, zirconia, aluminum phosphates, titanium phosphates, zirconium phosphates and silica-aluminas. The matrix is preferably alumina. The catalyst comprises at least one element of group VIII of the periodic table, preferably selected from among platinum and palladium, and it can also contain optionally at least one metal that is selected from among the metals of groups IIIA and IVA, preferably selected from among tin and indium and optionally sulfur.

The isomerization catalyst can comprise by weight relative to the total catalyst mass:

1 to 90% by weight of at least one EUO-structural-type zeolite, preferably 3 to 60% and even more preferably 4 to 40%, 0.01 to 2% by weight of at least one metal of group VIII, preferably 0.05 to 1%, optionally 0.01 to 2% of at least one additional element that is selected from groups IIIA and IVA of the periodic table, preferably 0.05 to 1%, optionally sulfur, a binder that ensures the make-up by weight to 100% of catalyst.

The catalyst that is used in the process according to the invention can be prepared by any method that is known to ones skilled in the art and in particular by those that are described in the prior art that relate to the catalysts that contain at least one EUO-structural-type zeolite and in particular the EU1, ZSM-50 and TPZ-3 zeolite.

The catalyst is preferably prepared as described in the patent application of the applicant FR-A-2 772 642. Thus, the catalyst preferably has a dispersion of the metal of group VIII that is between 50 and 100%, and more preferably between 60 and 100% and even more preferably between 70 and 100%, a macroscopic distribution coefficient of said metal of group VIII of between 0.7 and 1.3. The catalyst is preferably shaped in the form of balls or extrudates and has a mechanical resistance such that the bed crushing value is higher than 0.7 MPa, preferably between 0.8 and 1.2.

The isomerization zone is usually operated at a temperature of about 300° C. to 500° C., preferably about 320° C. to 450° C. and even more preferably about 350° C. to 420° C., at a partial hydrogen pressure of about 0.3 to 1.5 MPa, preferably about 0.4 to 1.2 MPa, at a total pressure of about 0.45 to 1.9 MPa, preferably about 0.6 to 1.5 MPa, at a PPH (feedstock weight/catalyst weight/hour) of about 0.25 $h^{-1}$ to 30 $h^{-1}$, preferably about 1 to 10 $h^{-1}$, and very often 2 $h^{-1}$ to 6 $h^{-1}$. The hydrogen that is introduced for the production of the isomerization can be recycled in said isomerization zone.

In a particular implementation of the isomerization stage, the isomerization zone can comprise a recycling as described in the patent application of the applicant, FR-A-2 777 275. The process then comprises at least one distillation zone downstream from the isomerization zone to recover, after the fraction that comprises the light compounds (with a boiling point less than 80° C.) is eliminated, a fraction that contains a majority of the aromatic compounds containing at least eight carbon atoms per molecule and that is sent into the xylene separation zone and so as to recover a fraction that comprises compounds with a boiling point of about 80° C. to 135° C. and more particularly at least one of the compounds that are selected from the group that consists of naphthenes with eight carbon atoms per molecule, the paraffins with eight carbon atoms per molecule, benzene and toluene, at least one of the compounds of said fraction, isolated from the entire fraction by treatment in at least one distillation zone, able to be recycled at the inlet of the isomerization zone. The percentage by weight of recycled compounds relative to the total feedstock that enters into the isomerization zone is between 0.01 and 20%. Actually, surprisingly enough, the fact of recycling at least one compound with a boiling point of between 80° C. and 135° C. makes it possible to decrease the parasitic reactions of the isomerization which, combined with the performance levels of the catalyst that is used within the scope of this invention, ensures considerable savings for the process. It is preferably possible to recycle the naphthenes with eight carbon atoms in the isomerization zone, whereby the other compounds of the fraction with a boiling point of between 80° C. and 135° C. such as toluene and paraffins can be recovered at this level of the process.

The output effluent of the isomerization zone that comprises the three isomers of the xylenes in a ratio that is essentially close to the one of the thermodynamic equilibrium is then either partly or totally recycled in the xylene separation zone after an optional treatment with earth (WO-96/20 907).

According to a preferred embodiment of the invention, a catalyst will be used that comprises an EUO-structural-type zeolite whose crystal size is smaller than 5 micrometers ($\mu$m), often less than 0.5 $\mu$m, and most often less than 0.2 $\mu$m. These crystals or crystallizates are often at least in part grouped in aggregates that have a grain size such that the value of Dv,90 is less than or equal to 500 $\mu$m, often less than 400 $\mu$m, most often less than 200 $\mu$m, and even more preferably less than or equal to 50 $\mu$m. The size of the aggregates is determined by grain size with laser diffraction. This measurement is taken on the zeolite powder that is suspended in water. After a first measurement, the suspension is subjected to ultrasound for thirty seconds, then a new measurement is taken. The ultrasound that is used is characterized by a power of 50 W and a frequency of 50 kHz. This procedure is repeated until the result no longer varies (at +5%). The volume-defined size distribution of the aggregates is calculated starting from light signals that are collected by detectors and with Fraunhofer's theory. Dv,X is defined as being the diameter of the equivalent sphere such that X% by volume of the aggregates has a size that is less than said diameter. These characteristics will be obtained directly during the synthesis of the zeolite and/or by any method that makes it possible to reduce the size of the aggregates, such as, for example, post-synthesis grinding or else a suitable kneading before shaping.

BRIEF DESCRIPTION OF THE DRAWING

The attached drawing is a schematic diagram.

DETAILED DESCRIPTION OF THE DRAWING

The invention will be better understood based on the diagram that illustrates in a nonlimiting manner the process and the device. The operating conditions of the adsorption are selected such that the first fraction that contains paraxylene is an extract and the second fraction that contains essentially metaxylene, orthoxylene and ethylbenzene is a raffinate. Via a line 1, a feedstock is conveyed that comprises about 18% of ethylbenzene, 18% of paraxylene, 45% of metaxylene and 17% of orthoxylene. A recycled effluent whose ethylbenzene content is considerably smaller, typically 7 to 13%, and whose paraxylene content is larger, typically 18 to 24%, is added at that point via a line 2. Another recycled effluent whose paraxylene content is larger, typically 40 to 70%, is introduced via a line 3. A line 4 recovers the feedstock and these two effluents; it conveys a mixture having the approximate composition: paraxylene 20 to 23%, ethylbenzene 8 to 14%, orthoxylene 19 to 22%, metaxylene 45 to 50%, which is introduced into a unit 8 for simulated countercurrent adsorption chromatography that comprises a limited number of columns and preferably a single column 6 that is filled with a zeolitic adsorbent, whereby the column or columns are divided into a limited number of sections (whereby the total number of column sections is between 9 and 15), and whereby the productivity that is expressed relative to the paraxylene that is produced is between 0.065 and 0.14 $m^3$ per $m^3$ of sieve and per hour expressed in ambient conditions. It is desorbed by toluene, at a rate of about 1.5 $m^3$ of toluene per $m^3$ of feedstock, whereby the operating temperature is approximately 165° C. A raffinate that is low in paraxylene and that contains basically toluene, metaxylene, ethylbenzene and orthoxylene is drawn off from this unit via a line 10, and an extract with a composition that is high in paraxylene and that contains basically paraxylene and toluene, whereby the major impurity is ethylbenzene, is drawn off via line 9. The raffinate is introduced into a distilling column 12 (top temperature 125° C., bottom temperature 160° C., for example) in which impure toluene or impure paraxylene is optionally recycled via a line 13 that is obtained from the washing unit of a crystallization unit that is specified below. At the top, toluene (about 40 to 45% of the amount that is introduced, for example) that contains, for example, less than 200 ppm of C8-aromatic fraction is drawn off via a line 14, and at the bottom of this column, a liquid (raffinate from which solvent is removed) that is high in ethylbenzene, metaxylene and orthoxylene and low in paraxylene (less than 0.6%, for example) that is sent into an isomerization unit 21 is drawn off via a line 15. This raffinate is brought into contact with the hydrogen that is introduced via a line 20 and with a catalyst with an EU1 zeolite base (with an Si/Al ratio, for example, equal to 18) and platinum to alumina (that comprises by weight, for example, 10%, 0.3% of platinum and 89.7% of alumina). A line 22 leads the isomerate from the outlet of the reactor to a distilling column 23 (top temperature 90° C., bottom temperature 160° C., for example). At the top, C1 to C5 hydrocarbons, hexane, cyclohexane are drawn off via a line 24, and at the bottom of this column, an effluent that contains 0 to 1% of benzene, 0 to 4% of toluene, 6 to 12% of ethylbenzene, 16 to 22% of paraxylene, 15 to 21% of orthoxylene, 41 to 46% of metaxylene and 2 to 10% of naphthenic and paraffinic components are drawn off via a line 25. This effluent enters a distilling column 26 that can separate at the top a naphthenerich fraction 80–135° C. that is recycled via line 27 to isomerization reactor 21. Via a line 2, the bottom fraction of column 26 that comprises less than 0.5% of paraffins and naphthenes is recycled to the adsorption liquid chromatography unit. The advantage of distilling column 26 and the recycling of naphthenes via line 27 is to reduce the losses of C8 aromatic compounds. Line 9 introduces the extract into a distilling column 16 from where toluene with less than 0.20% of C8-aromatic fraction (about 55 to 60% of the amount that is introduced for example) is drawn off at the top via line 17 and is recycled via. line 11 to the desorption solvent supply of the adsorption unit and optionally to the crystallization unit via line 18. At the bottom of column 16 at about 160° C., the low-purity paraxylene (at about 90% of paraxylene) is drawn off using a line 19 that leads it into a crystallization unit 5 that operates at about −10° C. In this unit 5, on the one hand, a solution or mother liquid that is low in paraxylene (typically 40 to 70%) is produced that is recycled via line 3 to the inlet of the liquid chromatography unit at the point where the feedstock is introduced, and, on the other hand, a paraxylene crystal cake that is saturated with mother solution is produced. This cake is centrifuged in a unit that is not shown in the figure and washed by toluene or by purified paraxylene. The washing toluene is brought via line 18 and, as shown in the figure, can come from the distillation unit of raffinate 12 and/or also from the distillation unit of extract 16. The toluene can also be obtained from recycling a portion of a portion of the toluene that is used for the washing that is described above. Remelted paraxylene with a purity of 99.8% is recovered from unit 5 via a line 28, and optionally impure toluene that is sent via line 13 to distillation 12 is recovered.

An embodiment is therefore described where the desorption solvent of the adsorption unit is either the sole solvent (if the paraxylene is recycled to wash the crystals) or optionally the same solvent as the one for washing the crystallization unit: toluene.

In the case where the paradiethylbenzene is the desorption solvent and the toluene is the washing solvent, distillation units 12 and 16 supply solvent only to the adsorption unit. An additional distillation element is then necessary to distill the toluene that is used in the washing unit of the crystallization unit. This essentially pure toluene is then recycled to the washing unit while the solution that is recovered at the distillation bottom is combined with the mother liquor and recycled to the adsorption unit via line 3.

All of the documents that are cited above in this description are incorporated as reference.

The simultaneous implementation of the obligatory means and the optional means extensively improve the operation of the process. The following example illustrates the operating conditions of the process and its performance levels.

EXAMPLE

The adsorption unit consists of 11 beds with a height of 1.05 m and one bed with a height of 0.7 m, and the common diameter of the beds is 0.9216 m; they are located in a single column. Each distributor plate is equipped with two separate lines that are connected to the outside, with one conveying the extract and the solvent and the second the feedstock and the raffinate. For each bed, four all-or-nothing valves make it possible to inject the feedstock or the solvent or to sample the extract or the raffinate. The column is charged with barium-exchange molecular sieve X whose grain size is between 0.4 mm and 0.8 mm in diameter. The operating temperature is 163° C., the pressure in the intake of the recycling pump is 10 bar absolute, and the pressure drop through all of the 12 beds is 7.5 bar. Injected is 7.73 m$^3$/h of a feedstock whose composition is (% by weight):

Paraffins and naphthenes: 1.959%
Toluene: 0.063%
Ethylbenzene: 10.385%
Paraxylene: 19.993%
Metaxylene: 43.361%
Orthoxylene: 21.546%
C9- and C10-aromatic compounds: 2.694%

Injected is 9.33 m$^3$/h of a desorbent whose composition is (% by weight):

Toluene: 99.009%
Ethylbenzene: 0.012%
Paraxylene: 0.013%
Metaxylene: 0.021%
Orthoxylene: 0.004%
Paraffins and naphthenes: 0.943%

Sampled under flow monitoring of 7.07 m$^3$/h is an extract whose composition is (% by weight):

Paraffins and naphthenes: 1.067%
Toluene: 76.894%
Ethylbenzene: 0.297%
Paraxylene: 21.106%
Metaxylene: 0.292%
Orthoxylene: 0.132%
C9- and C10-aromatic compounds: 0.211%

Sampled under pressure monitoring of 9.99 m$^3$/h is raffinate whose composition is (% by weight):

Paraffin and naphthenes: 1.644%
Toluene: 37.54%
Ethylbenzene: 7.881%
Paraxylene: 0.776%
Metaxylene: 33.542%
Orthoxylene: 16.67%
C9- and C10-aromatic compounds: 1.949%

The mean flow rate on the recycling pump is 33.2 m$^3$/h, while the switching time is 67.4 seconds. The water content that is measured by the Karl Fisher method is 130 ppm in toluene, and respectively 88 and 76 ppm in the extract and the raffinate. The paraxylene yield in the extract is 94.98%, the purity that is expressed relative to the C8-aromatic compounds is 96.7% and 94.1% after distillation of the solvent by counting the paraffins and naphthenes that are not distilled and the C9- and C10-aromatic compounds, and the productivity is 132 kg of paraxylene per m$^3$ of sieve and per hour.

The raffinate is distilled to eliminate the toluene that is reinjected into the adsorption unit. After distillation, the composition of the collected fraction is (% by weight):

Paraffin and naphthenes: 0.80%
Toluene: 1.21%
Ethylbenzene: 12.69%
Paraxylene: 1.25%
Metaxylene: 53.99%
Orthoxylene: 26.92%
C9- and C10-aromatic compounds: 3.15%

This raffinate, mixed with the naphthenes with eight carbon atoms, as well as the paraffins with eight carbon atoms and the toluene that are obtained from the isomerization effluent and recycled at the inlet of the reactor, is isomerized in the presence of a catalyst with a base of 10% of EU-1 zeolite of an Si/Al ratio of 18, 0.3% of platinum and 89.7% of alumina used as a binder at an operating temperature of 370° C., under a pressure of 8 bar and in the presence of hydrogen in an H$_2$/hydrocarbon molar ratio of 4.

The composition of the mixture at the inlet of the isomerization reactor is (% by weight):

Toluene: 1.62%
Naphthenes with 8 carbon atoms: 8.81%
Paraffins with 8 carbon atoms: 0.22%
Ethylbenzene: 11.57%
Paraxylene: 1.14%
Metaxylene: 49.23%
orthoxylene: 24.54%
C9- and C10-aromatic compounds: 2.87%

The isomerization effluent has the following composition (% by weight):

C6-: 0.69%
Benzene: 0.10%
Toluene: 1.88%
Naphthenes with 8 carbon atoms: 8.93%
Paraffins with 8 carbon atoms: 0.25%
Ethylbenzene: 6.94%
Paraxylene: 18.25%
Metaxylene: 40.18%
Orthoxylene: 19.69%
C9- and C10-aromatic compounds: 3.08%

The yield of C8-aromatic compounds is 98.37%, and the conversion of the ethylbenzene is 40.0%.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.968, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of at least one xylene isomer from a feedstock that comprises aromatic hydrocarbons with eight carbon atoms comprising the following stages:
   a) in at least one simulated moving-bed adsorption zone, a feedstock containing aromatic compounds with eight carbon atoms, including metaxylene, paraxylene, ethylbenzene and orthoxylene, is brought into contact continuously with a zeolitic adsorbent bed in the presence of a suitable desorption solvent, under adsorption conditions so as to obtain a first fraction containing solvent and high in desired isomer and a second fraction low in desired isomer and comprising the majority of the other isomers and solvent,
   b) the first fraction is distilled to separate the solvent from the desired isomer,
   c) the second fraction low in desired isomer is distilled to recover solvent, and a fraction containing the majority of the other isomers,
   d) the fraction that contains the majority of the other isomers recovered in stage c) is isomerized under suitable conditions in an isomerization zone in the presence of hydrogen and a catalyst comprising at least one EUO-structural-zeolite and at least one element of Group Vm of the periodic table,
   e) at least part of the recovered isomerate is distilled to obtain a fraction having a boiling point of about 80° C. to 135° C., and latter fraction is recycled, at least in part to the isomerization zone, and
   (f) at least part of the recovered isomerate is distilled to obtain a further fraction having a boiling point higher than 135° C. and said higher boiling point fraction is recycled, at least in part, to stage (a).

2. A process according to claim 1, wherein the desired isomer is paraxylene.

3. A process according to claim 1, wherein the desired isomer is metaxylene.

4. A process according to claim 1, wherein a crystallization of the desired isomer is initiated in at least one crystallization zone at a temperature of between +10° C. and −25° C., and, on the one hand, a mother liquor is obtained, and on the other hand, crystals of the desired isomer that are saturated with mother liquor are obtained.

5. A process according to claim 1, wherein the crystals of the desired isomer are washed with a suitable washing solvent, and the crystals are recovered.

6. A process according to claim 1, wherein the adsorbent of the simulated moving-bed adsorption zone that is used to extract specifically the paraxylene comprises at least one X zeolite or a Y zeolite whose exchangeable sites are occupied by alkaline or alkaline-earth cations.

7. A process according to claim 1, wherein the adsorbent of the simulated moving-bed adsorption zone that is used to extract specifically the metaxylene and the orthoxylene comprises at least one zeolite that is selected from among the X or Y zeolites that are exchanged with at least one of the following metals: Li, Na, Be, Mg, Ca, Sr, Mn, Cd, Cu, and Ni.

8. A process according to claim 1, wherein an adsorbent that incorporates a binder that is at least partly zeolitized is used in the separation zone.

9. A process according to claim 1, wherein the adsorbent of the simulated moving-bed adsorption zone has a spherical shape and a grain size of 0.4 to 0.8 millimeter in diameter.

10. A process according to claim 1, wherein water is injected into the adsorption zone to monitor water content on the weighted mean of the flow rates of extract and raffinate.

11. A process according to claim 1, wherein the EUO-structural zeolite that is contained in the isomerization catalyst is at least partly in acid form and comprises silicon and at least one element T that is selected from the group that is formed by aluminum, iron, gallium and boron, with an overall Si/T atomic ratio that is greater than 5, and optionally the EUO-structural zeolite is an EU1 zeolite.

12. A process according to claim 11, wherein element T of the isomerization catalyst is selected from the group that is formed by aluminum and boron.

13. A process according to claim 1, wherein the isomerization catalyst comprises at least one matrix that is selected from the group that is formed by clays, magnesia, aluminas, silicas, titanium oxide, boron oxide, zirconia, aluminum phosphates, titanium phosphates, zirconium phosphates and silica-aluminas.

14. A process according to claim 13, wherein the matrix of the isomerization catalyst is alumina.

15. A process according to claim 1, wherein the catalyst of the isomerization zone is in the form of balls or extrudates and has a mechanical resistance such that the bed crushing value is greater than 0.7 MPa.

16. A process according to claim 11, wherein the EUO-structural zeolite in the isomerization catalyst is at least in part in acid form, whereby the sodium content is such that the Na/T atomic ratio is less than 0.5.

17. A process according to claim 1, wherein the isomerization catalyst comprises by weight relative to the total catalyst mass:
   1 to 90% by weight of at least one EUO-structural zeolite,
   0.01 to 2% by weight of at least one metal of group VIII,
   a binder that ensures the make-up by weight to 100% of the catalyst.

18. A process according to claim 1, wherein the isomerization catalyst contains an EUO-structural zeolite whose crystal size is less than 5 micrometers ($\mu$m).

19. A process according to claim 18, wherein the crystals are at least in part grouped in aggregates that have a grain size such that the value of Dv,90 is less than or equal to 500 $\mu$m.

20. A process according to claim 11, wherein the zeolite is an EU1 zeolite.

21. A process for the production of at least one xylene isomer from a feedstock that comprises aromatic hydrocarbons with eight carbon atoms comprising the following stages:
   a) in at least one simulated moving-bed adsorption zone, a feedstock containing aromatic compounds with eight carbon atoms, including metaxylene, paraxylene, ethylbenzene and orthoxylene, is brought into contact continuously with a zeolitic adsorbent bed in the presence of a suitable desorption solvent, under adsorption conditions so as to obtain a first fraction containing solvent and high in desired isomer and a second fraction low in desired isomer and comprising the majority of the other isomers and solvent,
   b) the first fraction is distilled to separate the solvent from the desired isomer,
   c) the second fraction low in desired isomer is distilled to recover solvent, and a fraction containing the majority of the other isomers,
   d) the fraction that contains the majority of the other isomers recovered in stage c) is isomerized under suitable conditions in an isomerization zone in the presence of hydrogen and a catalyst comprising at least one EUO-structural-zeolite and at least one element of Group VIII of the periodic table,
   e) at least part of the recovered isomerate is distilled to obtain a fraction having a boiling point of about 80° C. to 135° C., and latter fraction is recycled, at least in part to the isomerization zone.

* * * * *

UNITED STATES PATENT AND TRADEMARK OFFICE
CERTIFICATE OF CORRECTION

PATENT NO. : 6,376,734 B1 Page 1 of 1
DATED : April 23, 2002
INVENTOR(S) : Magne-Drisch et al.

It is certified that error appears in the above-identified patent and that said Letters Patent is hereby corrected as shown below:

Column 13,
Line 25, "Vm" should read -- VIII --.

Signed and Sealed this

Fourth Day of January, 2005

JON W. DUDAS
*Director of the United States Patent and Trademark Office*